United States Patent [19]

Koyama et al.

[11] Patent Number: 5,334,786
[45] Date of Patent: Aug. 2, 1994

[54] PROCESS FOR PREPARING 1,1,1,2-TETRAFLUOROETHANE

[75] Inventors: Satoshi Koyama; Yukio Homoto; Naoki Esaka, all of Osaka, Japan

[73] Assignee: Daikin Industries, Ltd., Osaka, Japan

[21] Appl. No.: 9,420

[22] Filed: Jan. 27, 1993

Related U.S. Application Data

[63] Continuation of Ser. No. 912,139, Jul. 9, 1992, abandoned, which is a continuation of Ser. No. 668,121, Mar. 12, 1991, abandoned.

[30] Foreign Application Priority Data

Mar. 13, 1990 [JP] Japan .................... 2-61811
Oct. 22, 1990 [JP] Japan .................... 2-285596

[51] Int. Cl.$^5$ .................... C07C 17/00; C07C 17/08
[52] U.S. Cl. .................... 570/168; 570/165; 570/166; 570/167; 570/169
[58] Field of Search .................... 570/164, 167, 169, 165, 570/168, 166

[56] References Cited

U.S. PATENT DOCUMENTS

| | | |
|---|---|---|
| 2,885,427 | 5/1959 | Ruh et al. |
| 4,158,675 | 6/1979 | Potter .................... 570/169 |
| 4,605,798 | 8/1986 | Abel .................... 570/169 |

FOREIGN PATENT DOCUMENTS

| | | |
|---|---|---|
| 529154 | 8/1956 | Canada .................... 570/167 |
| 0295885 | 6/1988 | European Pat. Off. |
| 0331991 | 2/1989 | European Pat. Off. |
| 0328127 | 8/1989 | European Pat. Off. |
| 0408005 | 1/1991 | European Pat. Off. |
| 2108951 | 8/1972 | Fed. Rep. of Germany .... 570/169 |
| 2737950 | 3/1979 | Fed. Rep. of Germany .... 570/167 |
| 1307224 | 6/1969 | United Kingdom. |
| 1589924 | 9/1977 | United Kingdom. |
| 9008755 | 8/1991 | World Int. Prop. O. |

*Primary Examiner*—Alan Siegel
*Attorney, Agent, or Firm*—Birch, Stewart, Kolasch & Birch

[57] ABSTRACT

In a process for preparing 1,1,1-trifluorochloroethane by reacting, in a gas phase, trichloroethylene and hydrogen fluoride, when the reactant gases are diluted with a gas which is inactive to the reaction, it is very easy to control a reaction temperature, and when a generated gas from the reaction of 1,1,1-trifluorochloroethane and hydrogen fluoride is used as a diluent gas, generation of 1,1-difluoroethylene is suppressed to a very low level while not influencing the reaction between trichloroethylene and hydrogen fluoride.

7 Claims, 1 Drawing Sheet

PROCESS FOR PREPARING 1,1,1,2-TETRAFLUOROETHANE

This application is a continuation of application Ser. No. 07/912,139 filed on Jul. 9, 1992, now abandoned, which is a continuation of application Ser. No. 07/668,121 filed Mar. 12, 1991, now abandoned.

BACKGROUND OF THE INVENTION

1. Field of the Invention

The present invention relates to a process for preparing 1,1,1-trifluorochloroethane and 1,1,1,2-tetrafluoroethane. More particularly, the present invention relates to a process for preparing 1,1,1-trifluorochloroethane by reacting trichloroethylene and hydrogen fluoride and preparing 1,1,1,2-tetrafluoroethane by further fluorinating 1,1,1-trifluorochloroethane.

2. Description of the Related Art 1,1,1,2-Tetrafluoroethane (hereinafter referred to as "R-134a") is a promising substitute for dichlorodifluoromethane (R-12) which is widely used as a refrigerant, and it is highly desired to establish a process for producing R-134a. 1,1,1-Trifluorochloroethane (hereinafter referred to as "R-133a") is useful as an intermediate in the preparation of R-134a or a raw material for the preparation of trifluoroethanol.

Various processes are known for the preparation of R-134a but each process has its own advantages and disadvantages.

For example, in a process comprising reducing $CF_3CCl_2F$ (R-114a) with hydrogen, a conversion is high but a life of a catalyst is very short.

In a process comprising reacting trichloroethylene and hydrogen fluoride to obtain R-133a and then fluorinating R-133a with hydrogen fluoride in a gas phase (cf. Japanese Patent Kokai Publication No. 72105/1973), a selectivity is high and a life of a catalyst is long, but the process has the following drawbacks:

1. Since the reaction for fluorinating trichloroethylene is an exothermic reaction which generates a large amount of heat (about 30 Kcal./mole), control of the reaction is difficult.
2. Since, in the fluorination step of R-133a, 1,1-difluorochloroethylene (hereinafter referred to as "R-1122) which forms an azeotropic mixture with R-134a is contained in the reaction mixture, it is difficult to separate R-134a from the reaction mixture.

When R-134a is prepared by the above conventional process, the steps shown in FIG. 1 are employed.

In this process, trichloroethylene and hydrogen fluoride are supplied to a first reactor. A generated gas contains R-133a, unreacted hydrogen fluoride and hydrogen chloride. If the generated gas is introduced directly to a second reactor, R-134a is not produced due to unfavorable equilibrium. Therefore, the gas is introduced in a hydrogen chloride separator to remove hydrogen chloride from the gas. The remaining gas is then supplied to the second reactor and simultaneously a supplement amount of hydrogen fluoride is added. A reaction mixture from the second reactor comprises desired R-134a, unreacted R-133a and hydrogen fluoride, and a mixture of by-products containing R-1122. This reaction mixture is fed to a third reactor in which R-1122 is converted to R-133a, and the reaction mixture is supplied to a refining apparatus in which hydrogen chloride is separated and removed. The residual materials are supplied to a further refining apparatus to recover R-134a, and R-133a and hydrogen fluoride are recycled to the second reactor.

This process requires three reactors, in the first of which, R-133a is formed, in the second of which, R-134a is formed, and in the third of which, R-1122 is reduced. Therefore, the overall apparatus becomes expensive.

SUMMARY OF THE INVENTION

One object of the present invention is to provide a process for preparing 1,1,1-trifluorochloroethane with a simple apparatus at a low cost.

Another object of the present invention is to provide a process for preparing 1,1,1,2-tetrafluoroethane with a simple apparatus at a reduced cost.

According to a first aspect of the present invention, there is provided a process for preparing 1,1,1-trifluorochloroethane which comprises reacting, in a gas phase, trichloroethylene and hydrogen fluoride which are diluted with a gas which is inactive to the reaction.

According to a second aspect of the present invention, there is provided a process for preparing 1,1,1,2-tetrafluoroethane comprising reacting, in a gas phase, trichloroethylene and hydrogen fluoride to obtain 1,1,1-trifluorochloroethane and fluorinating 1,1,1-trifluorochloroethane with hydrogen fluoride to obtain 1,1,1,2-tetrafluoroethane, wherein trichloroethylene and hydrogen fluoride in the first step are diluted with a gas generated in the second step.

The present invention has been completed based on the finding that, when trichloroethylene and hydrogen chloride are diluted with the gas which is inactive to the reaction, it is very easy to control a reaction temperature, and when a generated gas from the reaction of R-133a and hydrogen fluoride is used as the diluent gas, generation of R-1122 is suppressed to a very low level while not influencing the reaction between trichloroethylene and hydrogen fluoride.

DETAILED DESCRIPTION OF THE INVENTION

Figure 1:
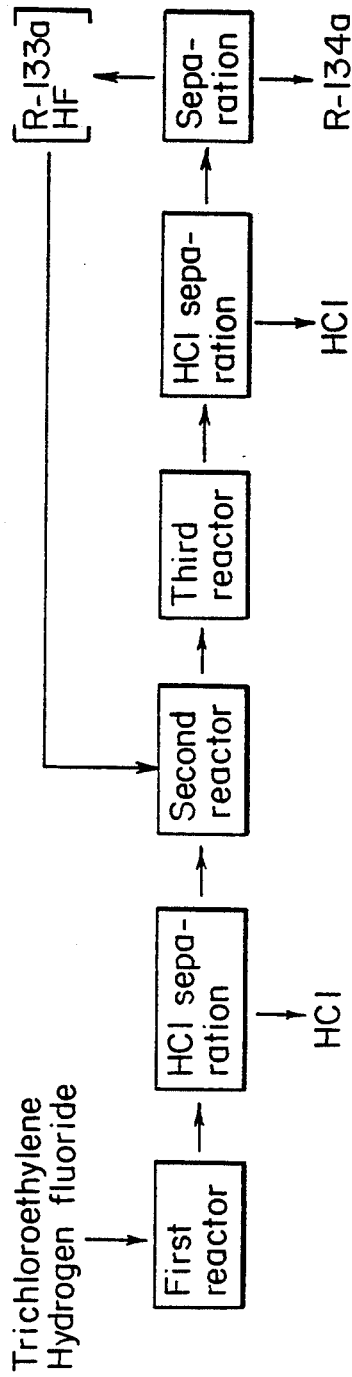
FIG. 1 is a flow chart of a conventional process for preparing 1,1,1-trifluorochloroethane.

The diluent gas which is inactive to the reaction serves to control the reaction temperature and its kind is not critical. Preferably, an inert gas such as nitrogen and argon is used. In particular, R-133a, R-134a and a mixture of them, which can be condensed and separated, are preferred. In addition, the diluent gas may contain a condensable gas such as hydrogen fluoride or hydrogen chloride. A composition of the diluent gas mixture is not limited.

The process of the present invention will be explained in detail.

To carry out the first reaction, trichloroethylene and hydrogen are supplied to a first reaction containing the diluent gas. When the diluent gas contains a sufficient amount of hydrogen fluoride, it is not necessary to supply hydrogen fluoride. An amount of hydrogen fluoride is from 3 to 100 moles per one mole of trichloroethylene. When the amount of hydrogen fluoride is smaller than the lower limit, an amount of unreacted trichloroethylene increases though the reaction may proceed. When the amount of hydrogen fluoride is larger than the upper limit, the reactor becomes large and the process becomes uneconomical.

An amount of the diluent gas is not critical. While the amount of the diluent gas has some influence on the control of reaction temperature, the reaction temperature can be controlled more or less. However, when a very large amount of the diluent gas is used, the reactor becomes large. Then, a volume of the diluent gas is usually from 1 to 40 times the volume of trichloroethylene.

The reaction temperature is preferably from 180° to 400° C. When R-133a, R-134a or a mixture of them is contained in the diluent gas, the reaction temperature is from 180° to 300° C. When the reaction temperature is higher than 300° C., R-134a reacts with hydrogen chloride which is generated from the reaction between trichloroethylene and hydrogen fluoride and is reconverted to R-133a.

The diluent gas may contain up to abut 25% by mole of R-1122. R-1122 is converted to R-133a in the presence of hydrogen fluoride. When an azeotropic mixture of R-1122 with R-134a is used as the diluent gas or added to the diluent gas, R-1122 is converted to R-133a whereby the amount of R-1122 is decreased. In this case, the reaction temperature is from 180° to 300° C. for the effective decrease of R-1122. When the reaction temperature is lower than 180° C., a reaction rate of trichloroethylene with hydrogen fluoride is small, and when the reaction temperature is higher than 300° C., R-1122 remains unconverted.

In the process of the present invention, a catalyst may be used. As the catalyst, any one that has a catalytic activity on the fluorination reaction can be used. In general, chromium oxide base catalysts are used. Examples are thermally treated $Cr(OH)_3$, fluorinated chromium oxide which is prepared by fluorinating thermally treated $Cr(OH)_3$ with hydrogen fluoride, a catalyst prepared by thermally treating a hydrate of $CrF_3$ in an oxygen-containing atmosphere, and the like.

In one of the most preferred embodiments of the present invention, a part or a whole of the generated gas from the second reaction is used as the diluent gas in the first reaction.

Figure 2:
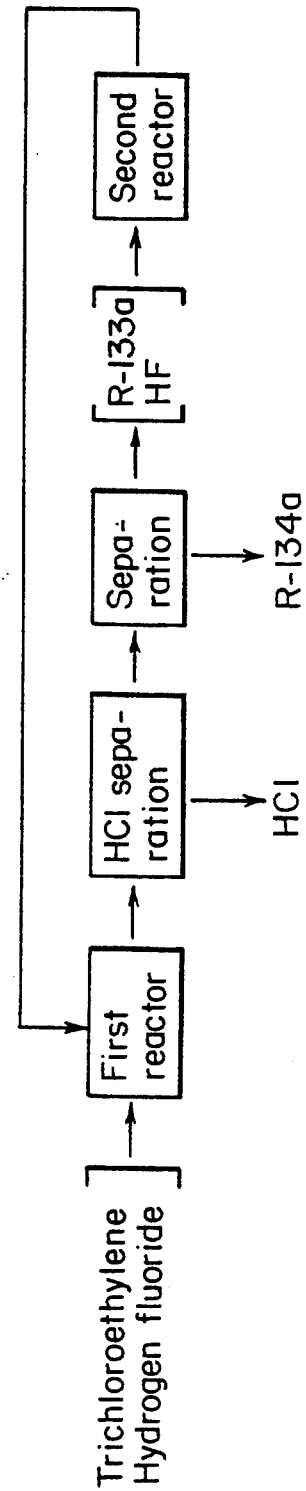
FIG. 2 is a flow chart of a process according to one embodiment of the present invention.

A flow chart of this embodiment is shown in FIG. 2.

In the second reactor, R-133a and hydrogen fluoride are supplied. The reaction product from the second reactor is a gaseous mixture of desired R-134a, unreacted R-33a and hydrogen fluoride, and by-products including R-122. The gaseous mixture is directly supplied to the first reactor together with the raw material, namely trichloroethylene.

Trichloroethylene reacts with hydrogen fluoride to form R-133a. Simultaneously, R-1122 reacts with hydrogen fluoride and is reconverted to R-133a. Therefore, the reaction mixture from the first reactor contains R-133a, R-134a, hydrogen fluoride, hydrogen chloride, a small amount of trichloroethylene and some by-products. But, the reaction mixture contains substantially no R-1122.

From the generated gas from the first reactor, hydrogen chloride is removed and then R-134a is separated. Remaining R-133a and hydrogen fluoride are supplied to the second reactor. To the second reactor, a supplemental amount of hydrogen fluoride is added.

In this process, since the heat generated in the first reaction is cooled by the reaction product from the second reaction, the reaction temperature in the first reaction is very easily controlled, and the number of the reactors can be decreased from three to two.

According to the volume of the first reactor, the generated gas from the first reactor contains a small amount of R-1122. In such case, a third reactor which is operated at a temperature of 180° to 300° C. is provided after the first reactor. Such third reactor may be a small one.

The reaction in each reactor will be explained.

To the second reactor, R-133a and hydrogen fluoride which is preferably anhydrous are supplied. A molar ratio of HF to R-133a is at least 2. Even when this ratio is smaller than 2, the reaction may proceed but the selectivity decreases unpreferably. The upper limit of this ratio is not limited. As this ratio increases, an amount of recovered and recycled hydrogen fluoride increases so that the production cost increases. In general, the upper limit of this ratio is about 10. To the second reactor, the same catalyst as above may be added.

The reaction temperature is preferably from 300° to 400° C. When the reaction temperature is lower than 300° C., the conversion is very low due to the equilibrium. When it is higher than 400° C., the selectivity is very low.

To the first reactor, a gaseous mixture of trichloroethylene, hydrogen fluoride and R-1122 is supplied. When the exit gas from the second reactor is directly supplied to the first reactor, trichloroethylene is simultaneously supplied in the same mole as that of R-133a which is consumed in the second reactor. Though hydrogen fluoride which reacts with trichloroethylene may be supplied, usually it is not necessary to supply hydrogen fluoride since the gas from the second reactor contains a sufficient amount of hydrogen fluoride.

The first reactor may contain the same catalyst as above.

The reaction temperature may vary with the activity of the catalyst. Usually, as described above, it is from 180° to 300° C.

Each reactor may be any type of a reactor. Since the reactions in the present invention are gas-solid contact reactions, usually, a multi-tubular fixed bed reactor or a fluidized bed reactor can be used. In addition, a moving bed reactor and the like may be used. The types of the first and second reactors may be the same or different.

PREFERRED EMBODIMENTS OF THE INVENTION

The present invention will be illustrated by following Examples.

COMPARATIVE EXAMPLE

By heating chromium hydroxide which was precipitated from an aqueous solution of chromium nitride with an aqueous ammonia, a fluorination catalyst was produced. Prior to use, the catalyst was fluorinated with hydrogen fluoride. Forty grams of the catalyst was filled in a Hastelloy C tube of 20 mm in inner diameter and 700 mm in length and heated to 320° C. in a nitrogen stream. Then, the supply of nitrogen was stopped and trichloroethylene and hydrogen fluoride were supplied at flow rates of 85 ml/min. and 420 ml/min., respectively. As soon as trichloroethylene and hydrogen fluoride were supplied, an exothermic reaction started and the maximum temperature reached 345° C.

After the produced gas was washed with water and dried, it composition was analyzed by gas chromatography.

The conversion of trichloroethylene was 98%, and the selectivity was 96%.

When the reaction was continued under the same conditions, sudden great decrease of the conversion was observed after 400 hours.

EXAMPLE 1

In the same manner as in Comparative Example but supplying nitrogen as a diluent gas at a flow rate of 1000 ml/min., the reaction and analysis were carried out. No heat generation was observed and the reaction temperature of 320° C. was maintained. The conversion of trichloroethylene was 98% and the selectivity was 97%.

When the reaction was continued under the same conditions, no sudden great decrease was observed even after 600 hours.

EXAMPLE 2

In the same manner as in Example 1 but using 10 g of the catalyst, supplying trichloroethylene and hydrogen fluoride at flow rates of 18 ml/min. and 90 ml/min., respectively, supplying a 1:1 mixture of R-133a and R-134a as a diluent gas together with the raw materials and keeping the reaction temperature at 250° C., the reaction and analysis were carried out. No heat generation was observed and the reaction temperature of 250° C. was maintained. The conversion of trichloroethylene was 98% and the selectivity was 97%.

EXAMPLE 3

Ten grams of the same catalyst as in Comparative Example was filled in a Hastelloy C tube of 20 mm in inner diameter and 700 mm in length (a second reactor tube) and heated to 360° C. in a nitrogen stream. Then, the supply of nitrogen was stopped and R-133a and hydrogen fluoride were supplied at flow rates of 60 ml/min. and 360 ml/min., respectively. The exit gas was washed with water and dried and its composition was analyzed by gas chromatography. The conversion of R-133a was 30%, and the selectivities of R-134a and R-1122 were 97% and 2%, respectively.

Ten grams of the same catalyst as above was filled in the same Hastelloy C tube (a first reactor tube) and heated to 250° C. in a nitrogen stream. Then, the supply of nitrogen was stopped and trichloroethylene was supplied at a flow rate of 18 ml/min. together with the exit gas from the second reactor tube to the first reactor tube. No heat generation was observed. The exit gas from the first reactor tube was analyzed by gas chromatography to find that the conversion of trichloroethylene was 99% and no R-1122 was detected. The amount of R-134a was not substantially changed.

What is claimed is:

1. A process for preparing 1,1,1,2-tetrafluoroethane which comprises the steps of:
   (1) reacting trichloroethylene with hydrogen fluoride in the gas phase in the presence of a fluorination catalyst to obtain 1,1,1-trifluorochloroethane in a first reaction zone,
   (2) introducing the reaction mixture from the first reaction zone to a second reaction zone,
   (3) reacting 1,1,1-trifluorochloroethane from the first reaction zone with hydrogen fluoride in the gas phase in the presence of a fluorination catalyst to obtain 1,1,1,2-tetrafluoroethane and by-produce 1,1-difluorochloroethylene in the second reaction zone,
   (4) recycling the entire reaction mixture including 1,1,1,2-tetrafluoroethane from the second reaction zone to the first reaction zone,
   (5) reacting 1,1-difluorochloroethylene produced in the second reaction zone with hydrogen fluoride to reduce the amount of 1,1-difluorochloroethylene in the first reaction zone, and
   (6) recovering 1,1,1,2-tetrafluoroethane ad hydrogen chloride formed as a by-produce from the reaction mixture from the first reaction zone between the first and second reaction zones.

2. The process according to claim 1, wherein the temperature in the first reaction zone is lower than the temperature in the second reaction zone.

3. The process according to claim 2, wherein the reaction temperature in the first reaction zone is from 180° to 300° C.

4. The process according to claim 2, wherein the reaction temperature in the second reaction zone is from 300° to 400°0 C.

5. The process according to claim 1, wherein the molar ratio of hydrogen fluoride to 1,1,1-trifluorochloroethane in the second reaction zone is from 2:1 to 10:1.

6. The process according to claim 1, wherein the required hydrogen fluoride s introduced into the second reaction zone.

7. The process according to claim 1, wherein the fluorination catalyst comprises thermally treated chromium hydroxide.

* * * * *